United States Patent [19]
Prent

[11] Patent Number: 5,364,580
[45] Date of Patent: Nov. 15, 1994

[54] BODY PART MOLD SYSTEM

[76] Inventor: Mark Prent, 35 Bank St., St. Albans, Vt. 05478

[21] Appl. No.: 885,458

[22] Filed: May 19, 1992

[51] Int. Cl.$^5$ .............................................. B29C 33/38
[52] U.S. Cl. .................................... 264/138; 249/157; 249/160; 264/223; 264/227; 425/2
[58] Field of Search ............... 264/138, 152, 163, 222, 264/223, DIG. 30, 225, 227, 313; 425/2; 249/55, 157, 160; 623/901

[56] References Cited

U.S. PATENT DOCUMENTS

| | | | |
|---|---|---|---|
| 384,448 | 6/1888 | Keller | 264/DIG. 30 |
| 1,504,822 | 8/1924 | Hess | 425/2 |
| 1,824,835 | 9/1931 | Pierce | 264/DIG. 30 |
| 2,761,443 | 9/1956 | Parker | 264/DIG. 30 |
| 3,563,234 | 2/1971 | Umstead | 264/222 |
| 3,769,392 | 10/1973 | Tessaro | 264/DIG. 30 |
| 3,896,202 | 7/1975 | Palau | 264/223 |
| 4,335,067 | 6/1982 | Castanis et al. | 264/225 |
| 4,735,754 | 4/1988 | Buckner | 264/222 |
| 4,812,273 | 3/1989 | Bevan | 425/417 |
| 4,828,116 | 5/1989 | Garcia | 264/313 |
| 5,121,835 | 6/1992 | Grupe | 425/803 |

FOREIGN PATENT DOCUMENTS

| | | | |
|---|---|---|---|
| 19999 | of 1913 | United Kingdom | 425/2 |
| 1025664 | 4/1966 | United Kingdom | 264/223 |

OTHER PUBLICATIONS

IBM Technical Disclosure Bulletin, vol. 12, No. 4, Sep. 1969.

Primary Examiner—Jay H. Woo
Assistant Examiner—Robert B. Davis
Attorney, Agent, or Firm—Thorpe North & Western

[57] ABSTRACT

The body part mold system includes a method of making accurate replicas of body parts, with the steps of the method comprising using an elongate prefabricated hollow transparent support form having an opening at one end and a slit on one side, inserting the body part through the opening into the form, sealing the slit so as to be leak-proof, pouring into the support form a liquid molding material containing alginate that rapidly sets to form a gelatinous matrix containing a negative impression of the body part, releasing the body part from the mold to leave a negative impression of the body part, casting a replica of the body part in the mold, and removing the replica from the mold. The method yields accurate replicas of body parts for medical, artistic, and other uses. The support forms may be either rigid or somewhat flexible, and are reusable. The transparency of the support forms permit precise positioning of the model or patient and monitoring of the filling of the form with molding material.

11 Claims, 2 Drawing Sheets

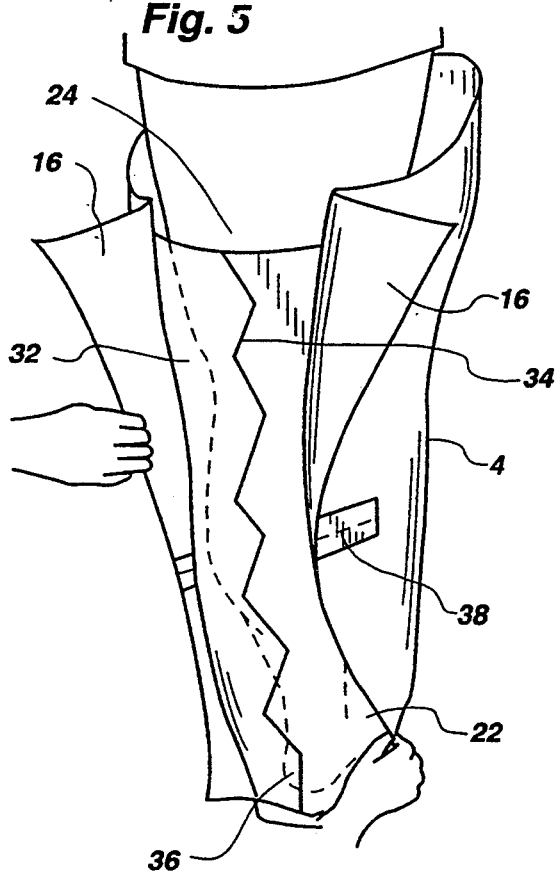
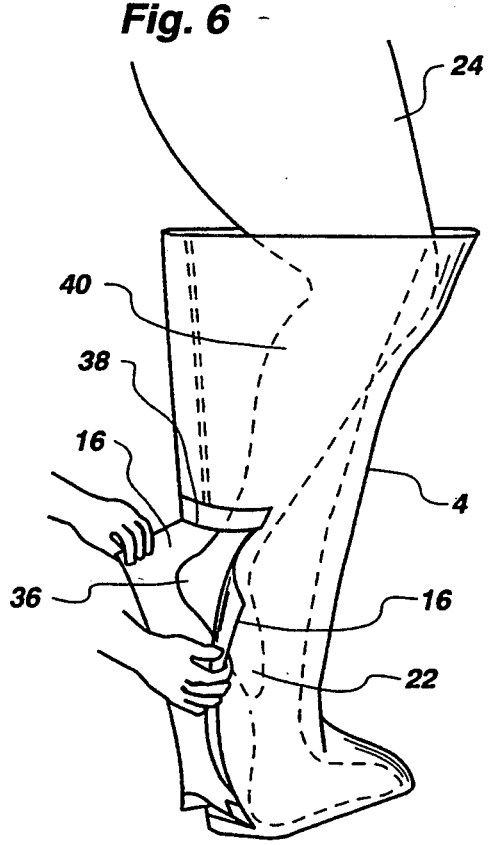
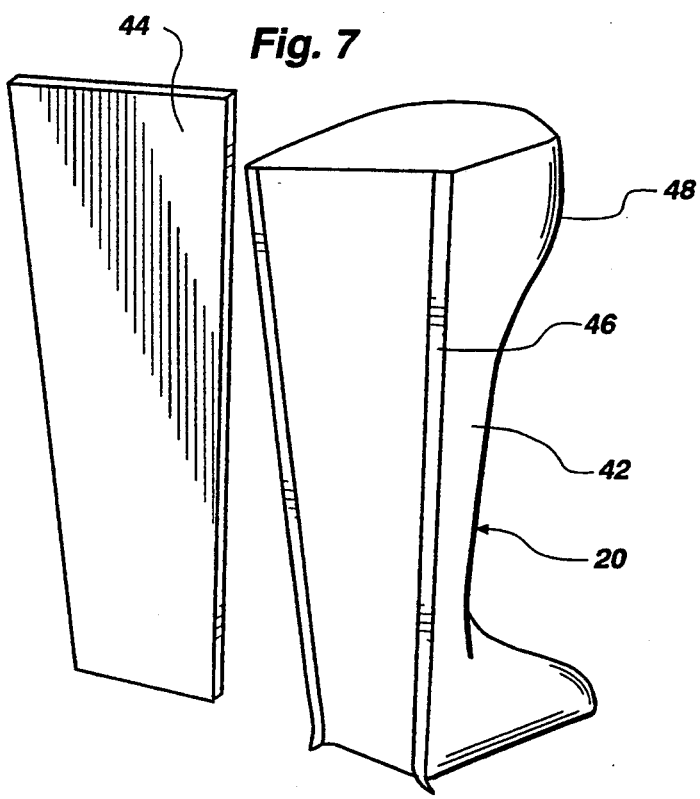

BODY PART MOLD SYSTEM

BACKGROUND OF THE INVENTION

This invention relates to a method and an apparatus for forming replicas of body parts. More particularly, this invention relates to a method of using a reusable apparatus to form molds of body parts from molding materials containing alginate and casting accurate replicas of the body parts.

Life-size, accurate replicas of body parts are used in a variety of fields, including medicine, art, and education. The conventional method of forming such replicas involves, first, forming a mold of the desired body part, for example of a leg, by wrapping the leg with plaster bandages, permitting the plaster to harden, cutting the bandages, and then prying the bandages away from the leg. The plaster bandages are then used as a mold for casting a replica of the leg, after which the bandages are removed and discarded. One problem with this is that when the plaster bandages are removed from the leg of a patient or model, there is necessarily some distortion of the plaster and this results in a replica which is not exactly the same shape as the leg being modeled. Further, preparing the bandages, wrapping them about the body part, and then removing them is both time-consuming and messy. Finally, after the replica is cast, the plaster bandages must be discarded, being unsuitable for repeating the casting process. The process is thus wasteful of time, materials, and effort.

One proposal for improving the conventional plaster bandage method of constructing molds involves encasing the body part with padding material, coating the padding material with petroleum jelly to prevent adhesion, and wrapping the padded body part with plaster bandages (U.S. Pat. No. 4,735,754). After the plaster drys and hardens, the plaster bandages are cut and removed from the padded body part, then the padding material is removed and the body part is placed in the plaster bandage again. Alginate or other molding material is poured into the plaster form and permitted to set. The body part is then removed, leaving an impression of the body part in the alginate mold. This system of forming molds suffers from several disadvantages. First, the plaster form is not reusable, thus, if a mold of a different patient or model were desired, a new plaster form would need to be constructed. Second, this process is clumsy and time-consuming. The patient or model must endure two casting procedures: (1) being wrapped in padding material, having the plaster bandages applied, waiting for the plaster to dry and harden, and having the plaster form being removed, and (2) casting the alginate impression. Third, the system relies on custom-fitting the plaster form for each individual patient or model. Fourth, the system is less useful for making molds of an entire leg than of a mere foot. This is due to the cracks and distortions that are introduced in the plaster form in removing it from the padded body part. The problems with cracks and distortions increase as the size of the body part increases. Since the alginate impression also relies on the plaster form or general support and shape, the accuracy of the alginate impression depends on the plaster form. Fifth, a plaster form for making a mold of an entire leg would need to be thick enough to support the 25-40 pounds of alginate used in making the impression. Increased thickness of the plaster form would require more time to dry and harden. Further, a thick plaster form would be more susceptible to cracking and distortion in removal from the padded body part.

OBJECTS AND SUMMARY OF THE INVENTION

It is an object of the present invention to provide a method of forming accurate replicas of body parts in a quick, inexpensive, and simple fashion.

It is also an object of the invention to provide a method of forming body part molds that yield accurate impressions of the body part with minimal traces of seam lines.

It is another object of the invention to provide reusable, prefabricated support forms for making body part molds.

It is a further object of the invention to provide such prefabricated support forms that may be made of transparent materials so that the patient or model can be optimally aligned in the support form, and the mold constructed.

It is still another object of the invention to provide such support forms which allow for easy and gentle release of the hand or foot of a person whose body part is being used to construct the mold.

These and other objects may be accomplished by using prefabricated plastic support forms to construct body part molds by making alginate impressions of the body part. A body part is inserted into the support form so that there is an approximately uniform space of about 1.5 inches between the body part and the interior of the form. Once the body part is positioned in the support form, a mold-forming material such as alginate, is poured into the support form and permitted to set. Then the patient or model is released from the mold and the replica body part can be cast using traditional materials such as plaster or wax. The replica is then released from the mold and the support form can be reused for forming new molds, since it is undamaged by the process.

BRIEF DESCRIPTION OF THE DRAWINGS

FIG. 5 shows the rear flaps of the flexible support form of FIG. 1 spread apart and a cut in the alginate mold through which the model can withdraw the leg.

FIG. 6 illustrates spreading of the lower portion of the rear flaps of the flexible support form of FIG. 1 so that the model can push the heel of the foot through a cut in the back of the alginate mold and lift the foot to free the leg from the mold.

FIG. 7 shows a rear perspective view of two-piece rigid support form for making leg molds, in accordance with the present invention.

DETAILED DESCRIPTION OF THE INVENTION

Figure 1:
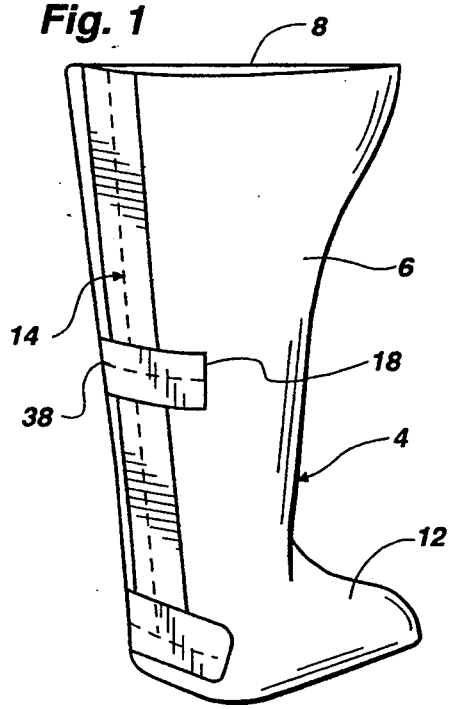
FIG. 1 shows a rear perspective view of a one-piece flexible support form for making replicas of a leg, in accordance with the present invention.
Figure 2:
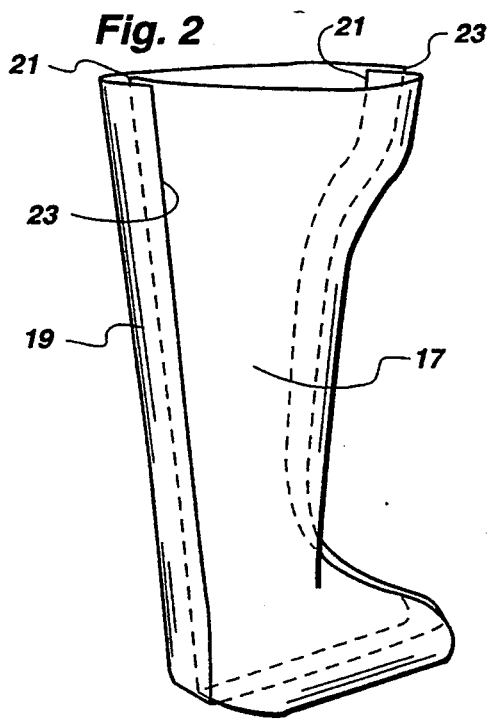
FIG. 2 illustrates a flexible support form made of two sections for constructing molds of various sizes, in accordance with the present invention.

Referring to the drawings, the steps in preparing a replica of a body part according to the invention are shown. For purposes of example only, the method will be described in connection with making a replica of a right leg. FIGS. 1–7 illustrate the advance in the process of fabricating an accurate replica of a body part, including all the features and characteristics of the model.

FIG. 1 shows the shape of a flexible, one-piece support form 4 for making a replica of a leg. This embodiment of the invention includes an upright hollow body or section 6, with an opening 8 at the upper end, and a hollow section 12 extending forwardly from the lower end of the section 6. A slit 14 is formed on a side of the section 6 opposed to the forwardly extending hollow section 12. The slit 14 extends from the opening 8 the length of the side of the section 6. Overlapping flaps 16 (FIG. 3) are located on opposing sides of the slit 14 to permit spreading apart of the flaps 16 and to allow sliding in and out of the body part. These flaps 16 are closed and sealed with tape 18 or other sealant to enclose the body part within the support form 4 and make the support form 4 leak-proof.

The flexible plastic support form 4 may be prefabricated from vinyl or some other flexible transparent plastic in small, medium, and large sizes to accommodate the size of body parts of most patients or models. Alternatively, one size of support form 4 can be used to make a mold for accommodating various sizes of a body part by cutting the support form 4 along a generally vertical locus to yield generally mirror-image halves as in FIG. 2. The two halves 17 and 19 can then be placed together, with the continuous edge 21 of one half fitted or nested within the continuous edge 23 of the other and moved toward or away from the other half to thereby vary the cross-sectional area (size) of the mold.

The flexible support form 4 is advantageous for making replicas of body parts of patients or models with limited mobility because the rear flaps 16 can be spread apart to permit easy access to the interior of the support form 4. One-piece flexible support forms 4 are quite inexpensive, also. Rigid two-piece support forms 20, shown in FIG. 7, constitute another embodiment of the invention and have the advantage of greater sturdiness than the flexible type.

Figure 3:
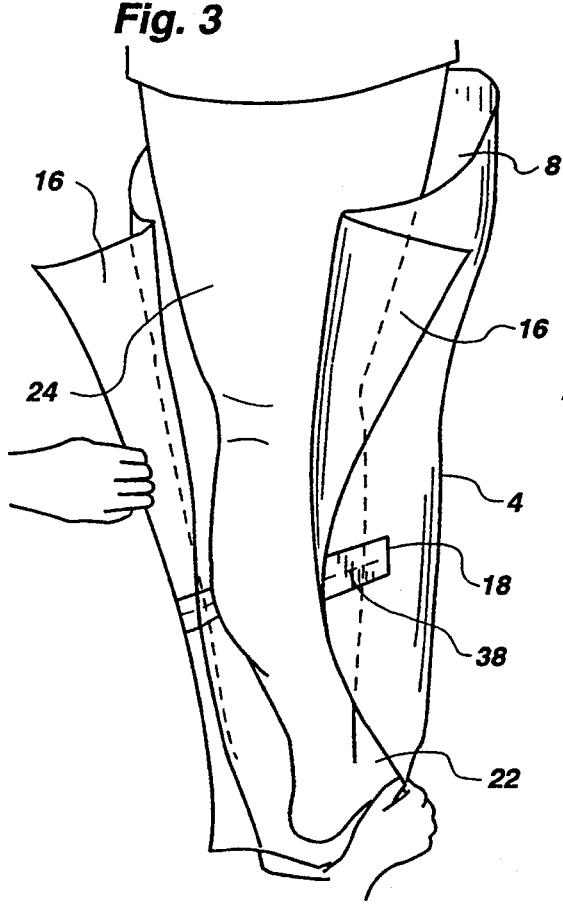
FIG. 3 illustrates a leg in position in the flexible support form of FIG. 1 with the opposing flaps spread apart.

FIG. 3 shows how a model or patient placing the foot 22 and leg 24 into the support form 4 by spreading apart the overlapping flaps 16 at the rear of the support form 4. After the foot 22 and leg 24 are in position, the flaps 16 are closed by overlapping and sealing them with tape 18 or other sealant. A model or patient with reduced mobility would find it easy to be properly positioned in this way. Alternatively, the support form 4 can be sealed and then the model or patient can insert a foot 22 and leg 24 into the support form 4 through the top opening 8.

Figure 4:
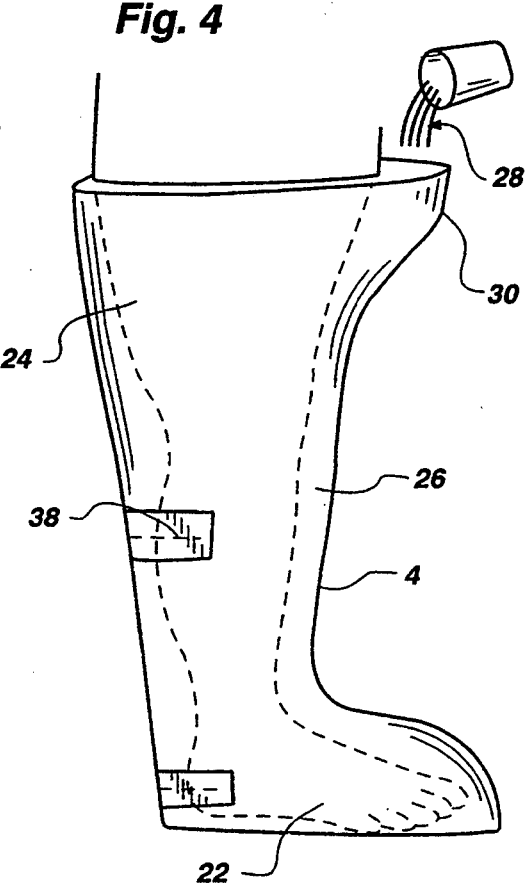
FIG. 4 shows a side elevational view of the flexible support form of FIG. 1 with a leg disposed therein, and showing the space between the leg and the support form into which the molding material is poured.

FIG. 4 shows that after the foot 22 and leg 24 are properly positioned in the support form 4 there should be about 1.5 inches of space 26 between the leg 24 and the support form 4. Into that space 26 is poured the liquid molding material 28 containing alginate. This amount of space permits construction of an alginate mold that is thick enough to be partially self-supporting, has enough flexibility to permit easy removal of the model's leg, has a "memory" to return to the proper spatial configuration with only minimal manipulation, and is not unnecessarily wasteful of materials. At the top of the support form 4 the space between the leg 24 and the support form 4 is wider than elsewhere to serve as a funnel 30 for pouring in the molding material 28. The liquid alginate sets into a gelatinous matrix within a few minutes.

The support form 4 is then opened by removing the tape 18 or other sealant and spreading apart the edges of the flaps 16 as in FIG. 5. The alginate mold 32 is then cut along the line 34 from the heel 36 to the back of the leg 24 to permit the model or patient to remove the foot 22 and leg 24. The alginate mold 32 is easily cut with an instrument such as a sculptor's spatula. Another method of cutting the alginate mold is to pull a string, such as dental floss, that was taped to the model's or patient's leg before forming the mold. As the string is pulled it cuts through the mold. The alginate does not stick to the skin of the patient or model. However, if there is hair on the body part, especially if the hair is more prominent than fine down, petroleum jelly may need to be applied to the model's skin before the process begins so that the alginate does not stick to the hair and disrupt the alginate mold when the body part is removed from the mold.

It is not necessary to cut the alginate mold 32 from heel 36 to the top of the mold to release the model or patient, as shown in FIG. 6. A horizontal slit 38 may be fashioned in the rear flaps 16 about mid way between the top and bottom of the support form 4 to permit the flaps 16 below the horizontal slit 38 to be spread apart while the leaving sealed the upper section of the support form 4. Then the portion of the alginate mold that is exposed can be cut from heel 36 to calf 40. The heel 36 is withdrawn through the cut portion of the mold and the foot 22 raised. Then, the foot 22 is straightened and the foot 22 and calf 40 are withdrawn upwards through the impression left in the alginate by the leg 24.

It is not always necessary to cut the mold to release the body part. For example, if only a foot or hand is the subject of the process, the foot or hand can be wiggled to permit air to enter between the body part and the mold to release the suction that tends to hold the body part in the mold. Then the foot or hand can be drawn out of the mold because the alginate is flexible enough to permit the foot or hand to be drawn out through the smaller cavity created around the ankle or wrist. Then the mold will return to the correct position because of its "memory."

After the body part is removed from the mold, the mold is manipulated back into its proper spatial configuration. This manipulation is minimal because of the "memory" of the alginate returns it to the same spatial configuration it had when it set. The support form is then reclosed around the alginate mold. Then the mold is ready for casting of the replica by traditional means. Plaster, wax, and other media may be used in casting the replica. After hardening of the cast replica, it is removed for final finishing. Alginate, when it is set but still moist, does not stick to most hard surfaces, including the plastic support form and the replica body part.

The process is the same as described above, with only minor variations, when a rigid two-piece support form 20 is used instead, as in FIG. 7. A rigid support form 20 is constructed in pieces which fit together and are sealed to form a leak-proof hollow vessel with an opening at one end into which the body part is placed. The preferred embodiment of the rigid transparent plastic design for modeling a leg is comprised of a front section 42 for surrounding the front and sides of the leg and foot and the bottom of the foot, and a rear section 44 for surrounding the rear of the foot and leg. The rear section 44 clamps to a flange 46 which is integrally part of the rear edge of the front section 42. Clamping the sections together seals the support form 20. After the foot and leg are inserted and properly positioned, about 1.5 inches of space remains between the leg and the support form 20. Into this space the molding material may be poured and the mold formed as described above for the flexible support form design. The rigid support form 20 also includes a funnel 48 at the top of the front section 42.

This body part mold system is more efficient and easier than traditional methods of making molds. Another advantage is that the transparent plastic support form permits the artist or technician to observe the position of the body part within the form and instruct the model or patient to shift position if needed. If only a part of a leg or other body part must be molded, the clear plastic of the support form permits observation of the fill-level as the alginate is poured.

Another advantage of this system is that distortion is less than with traditional methods. Impressions taken in plaster bandages are irreversibly distorted when the body part is removed. Alginate, however, because of its "memory" returns to the same position as when the body part was in place. An important advantage for artists is that seam lines are minimal, though not totally eliminated if the alginate mold was cut to release the body part during mold formation.

Another advantage of this system is that the support forms may be prefabricated in small, medium, and large sizes to accommodate almost any patient or model. Only if a person were very large or very small would a special support form be needed.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

I claim:

1. A method of fabricating replicas of body parts of a model or patient, comprising the steps of:
   (a) inserting the body part into a one-piece flexible support form shaped to enclose the body part, with one portion of the form having an opening to allow insertion of the body part therethrough, the support form being large enough to leave a substantially uniform space of about 1.5 inches between the exterior of the body part and the interior of the support form and having a slit formed on a side of the form to extend from the opening the length of said side, with overlapping flaps located on opposing sides of the slit to selectively spread apart and allow sliding out of the body part and to seal and enclose the body part;
   (b) forming a negative impression mold of the body part by pouring a liquid molding material of alginate and water into the space between the body part and the support form, and permitting the material to set into a gelatinous matrix;
   (c) removing the body part from the mold;
   (d) casting a positive replica of the body part by pouring a replica-forming material into the negative impression left in the mold; and
   (e) removing the positive replica from the alginate mold and support form.

2. The method of claim 1 further including providing a support form comprised of a transparent material.

3. The method of claim 2 wherein step (c) comprises spreading apart the overlapping flaps, cutting the mold along the length of a side of the mold, and withdrawing the body part through the cut in the mold.

4. The method of claim 2 wherein step (c) comprises spreading apart a lower portion of the overlapping flaps, cutting the mold at a lower end that is exposed by spreading apart the flaps, laterally withdrawing a portion of the body part through the cut in the mold, then raising and withdrawing the body part through the top of the mold.

5. A method of fabricating replicas of body parts of a model or patient, comprising the steps of:
   (a) providing a support form shaped to enclose the body part, with one portion of the form having an opening to allow insertion of the body part therethrough, the support form being comprised of two sections separable along a generally vertical locus to define opposing continuous free edges of the sections and fittable together to enclose the body part, wherein the continuous edge of one section is dimensioned to enable it to fit within the continuous edge of the other section and slide toward and away from the other section for changing the cross-sectional area of the support form;
   (b) inserting the body part into the support form, sliding the two sections in relation to each other to leave a substantially uniform space of about 1.5 inches between the exterior of the body part and the interior of the support form, and sealing the support form to enclose the body part;
   (c) forming a negative impression mold of the body part by pouring a liquid molding material of alginate and water into the space between the body part and the support form, and permitting the material to set into a gelatinous matrix;
   (d) removing the body part from the mold;
   (e) casting a positive replica of the body part by pouring a replica-forming material into the negative impression left in the mold; and
   (f) removing the positive replica from the alginate mold and support form.

6. A support form for fabricating body part molds comprising
   a hollow body made of a thin transparent material, open at one end to allow insertion of a body part, and having an elongate slit on one side of the body part with flexible overlapping flaps for selectively covering or opening the slit, said hollow body being formed to surround the body part while leaving a space between the hollow body and the body part,
   means for sealing the flaps when in the overlapping position to form a leak-proof vessel for receiving a molding material, and
   funnel means formed at the opening of the hollow body for receiving molding material into the space between the hollow body and the body part.

7. The support form according to claim 6 wherein the hollow body comprises a vertical hollow cylinder with a laterally extending hollow section for receiving a leg and foot, wherein the slit is formed at the rear of the cylinder, opposite the location of the hollow section, and wherein the sealing means comprises adhesive tape.

8. A support form for fabricating body part molds comprising
- two sections made of substantially rigid transparent material, with the sections being joinable to define a hollow therein and an opening on one end to receive the body part, wherein one of the sections includes a front section for surrounding the front, sides, and end of the body part, and wherein the other section includes a back section for surrounding the back of the body part,
- means for sealing the two sections together to form a leak-proof vessel into which a molding material may be poured, wherein the sealing means comprises a flange integrally molded as the rear edge of the front section and to which the rear section is clamped, and
- funnel means formed in the front section at the opening for receiving molding material into the space between the support form and the body part.

9. The support form according to claim 8 wherein the front section is formed to surround the front and sides of the foot and leg and the bottom of the foot, and the back section is formed to surround the back of the foot and leg.

10. A method of fabricating replicas of body parts of a model or patient, comprising the steps of:
(a) inserting the body part into a support form shaped to enclose the body part, wherein the support form is comprised of two sections of substantially rigid transparent material with the sections being joinable to enclose the body part, including means for sealing the two sections together to form a leak-proof vessel into which a molding material may be poured wherein the sealing means comprises a flange integrally molded as an edge of one of the sections to which the rear section is clamped, with one portion of the form having an opening to allow insertion of the body part therethrough and said opening forming funnel means for receiving liquid molding material, the support form being large enough to leave a substantially uniform space of about 1.5 inches between the exterior of the body part and the interior of the support form;
(b) forming a negative impression mold of the body part by pouring a liquid molding material of alginate and water into the space between the body part and the support form, and permitting the material to set into a gelatinous matrix;
(c) removing the body part from the mold;
(d) casting a positive replica of the body part by pouring a replica-forming material into the negative impression left in the mold; and
(e) removing the positive replica from the alginate mold and support form.

11. The method of claim 10 wherein one of the sections comprises a front section surrounding the front and sides of a person's leg and foot, and the bottom of the foot, and wherein the other section comprises a rear section joinable to the front section to allow for enclosing the person's leg and foot.

* * * * *